United States Patent
Hamada (10) Patent No.: US 7,349,810 B2
(45) Date of Patent: Mar. 25, 2008

(54) SAFETY TEST SUPPORT SYSTEM, METHOD AND PROGRAM

(75) Inventor: Takaharu Hamada, Osaka (JP)

(73) Assignee: H & T Corporation, Osaka (JP)

( * ) Notice: Subject to any disclaimer, the term of this patent is extended or adjusted under 35 U.S.C. 154(b) by 486 days.

(21) Appl. No.: 10/786,321

(22) Filed: Feb. 25, 2004

(65) Prior Publication Data

US 2005/0143925 A1    Jun. 30, 2005

(30) Foreign Application Priority Data

Dec. 25, 2003   (JP)   .............................. 2003-429897

(51) Int. Cl.
 *G06F 7/00* (2006.01)
(52) U.S. Cl. ........................... 702/19; 702/20; 703/11; 707/102
(58) Field of Classification Search ................ 364/184; 702/19, 29
 See application file for complete search history.

(56) References Cited

U.S. PATENT DOCUMENTS 5,448,720 A  *  9/1995  Uriu et al. .................. 710/240
5,784,274 A  *  7/1998  Murayama et al. ........... 700/79

FOREIGN PATENT DOCUMENTS

| JP | H07-110325 | 4/1995 |
| JP | H10-275093 | 10/1998 |
| JP | 2001-116744 | 4/2001 |
| JP | 2001-188680 | 7/2001 |

OTHER PUBLICATIONS

Tox Launcher—Advertisement/Information Sheet, 2007.
Functions and Developments of TOX-LAUNCHER—Author: Takaharu Hamada—Updated Feb. 2005.
21 CFR Part 58, 2007.
Guidance for Industry—Part 11, Electronic Records; Electronic Signatures—Scope and Application—Aug. 2003 Pharmaceutical CGMPs.
Part 11—Final Rule and Discussion, 1997.

\* cited by examiner

*Primary Examiner*—Mary K Zeman
(74) *Attorney, Agent, or Firm*—Wood, Phillips, Katz, Clark & Mortimer (57) ABSTRACT

A safety test support system comprises application storage 5, an application activating means 7, check program storage 17 and an inspection conducting means 19. The application storage 5 stores applications for safety tests, which are functionally partitioned according to data items and/or operations. The application activating means 7 activates at least one application selected from the applications. The check program storage 17 stores check programs each for detecting a change or changes in one of the applications during the system operation. The inspection conducting means 19 detects the changes in the applications by sequentially executing the stored check programs in response to an inspection conducting signal. Accordingly, the support system carries out an inspection to automatically detect the changes during the system operation so that the system can comply reliably with the GLP and other standards.

6 Claims, 5 Drawing Sheets

SAFETY TEST SUPPORT SYSTEM, METHOD AND PROGRAM

FIELD OF THE INVENTION

The present invention relates to a safety test support system, a safety test support method and a safety test support program, which may be applied to the chemical test data management for recording, managing and accumulating, compiling or tabulating data on living bodies to which mainly chemicals have been given. The data include body weight, food consumption, water consumption, biochemical test results, clinical symptom (or condition) observation results, pathological opinions (findings or observations), urinary output, ophthalmologic test results, hematological test results, etc. In particular, the system, method and program are suitable for chemical toxicity tests on animals.

BACKGROUND OF THE INVENTION

Before medicines, pharmaceuticals, agricultural chemicals, food additives and other chemicals are marketed, they are clinically tested for the safety of human bodies from carcinogenicity, toxicity, etc. Prior to the clinical tests, the safety is confirmed by means of non-clinical tests on animals such as rats and mice.

The non-clinical tests include a single dose toxicity test, a repeated dose toxicity test, a reproduction/generation toxicity test, and a mutagenicity test. The single dose toxicity test proves the amounts in which a chemical is toxic if it is given once in these amounts to an animal. This test also proves what characterizes the toxicity of the chemical. The repeated dose toxicity test proves the amounts in which a chemical is toxic if it is given two or more times in these amounts to an animal. This test also proves the amounts in which the chemical is nontoxic if it is given two or more times in these amounts to the animal. This test further proves what characterizes the toxicity of the chemical. The reproduction/generation toxicity test reveals the influences of a chemical on animal reproduction and generation. The mutagenicity test proves whether a chemical contains a substance that may cause a DNA lesion, and whether the chemical induces a mutation. The non-clinical tests also include a carcinogenicity test, a skin sensitization test, a skin photosensitization test and a dependence test.

Each of the non-clinical tests includes the steps of actually giving the animal the chemical, measuring the animal's body weight, food consumption, water consumption, urinary output, etc., observing the animal's clinical condition etc., making histopathological observations etc. about the animal, and accumulating, compiling or tabulating and analyzing the obtained data.

The non-clinical tests are conducted prior to the clinical tests, where the chemicals are actually given to human bodies. Since the chemicals eventually affect the human bodies, it is necessary to accurately understand and analyze the influences of the chemicals on living bodies. For this purpose, computer systems have been used to record, manage and analyze data (for example, Japanese Unexamined Patent Publication No. H07-110325).

As stated above, medicines, pharmaceuticals and other chemicals influence human bodies. This i s why the Health, Labor and Welfare Ministry and other Japanese government offices have set up strict standards of data management to prevent the foregoing safety test data from being altered dishonestly. The standards are known generally as GLP (good laboratory practice). As a matter of course, the computer systems that manage the data need to satisfy the GLP standards.

Needless to say, the design itself of the computer systems needs to meet the GLP standards. The application of the computer systems is very costly because the market for them is very niche, and because the application needs special know-how. When the computer systems are installed, it is necessary to confirm whether they work reliably in compliance with the GLP standards. After the system operation starts, the computer systems may be partially upgraded. In this case, it is necessary to confirm again that the whole systems work reliably in compliance with the GLP standards, and to record the confirmation in writing. It is also necessary to guarantee that the systems themselves have not been tampered with.

Each of the conventional computer systems is installed and operated with all functions integrated into it, and the whole system complies with the GLP and other standards. For this reason, even if a limited part of the system functions is upgraded, the whole system needs to be tested again for operation. For example, in recent years, because virus programs and other system destruction programs have been spreading through security holes, operation system makers have frequently been providing security patches. For safe system operation, it is essential that the computer systems be updated as soon as the security patches are provided.

As stated above, all functions are integrated into each of the conventional computer systems, and the whole system complies with the GLP and other standards. Consequently, even if a security patch is applied only to the operation system of the computer system, the whole computer system is regarded as upgraded and accordingly needs to be tested for validation. Validation usually takes two to three people three or more months. When the computer system is installed, it undergoes a general acceptance inspection. Once the computer system starts operating, however, it is practically impossible to carry out the subsequent validation required after the functions etc. of the system are updated. There is no real method of operation but continuing the system operation without updating and/or upgrading the computer system so that the validation can be avoided.

In the circumstances, even if a security hole is detected during the system operation, a security patch cannot be applied, but the system operation is continued with anxiety for system safety. The software itself of the computer system can be used with general purpose hardware. However, if the hardware operated as a general purpose computer, validation would be required by the updated operation system and the other updated applications that are not cooperative with the newly installed software. This substantially requires the provision of a special purpose computer, consequently making the installation cost very high.

Various conventional validation systems are disclosed (for example, Japanese Unexamined Patent Publication No. H10-275093). Because the validation systems are mainly used to find and correct bugs in programs under development, they detect even slight changes in the results of the validation and output N.G. (error) signals. If the validation systems are applied to the safety test support systems in operation, they may detect even slight changes of fonts and display color as bugs and/or alterations and output N.G. signals. Because these slight changes do not at all affect the operation of the support systems in compliance with the GLP and other standards, all the output N.G. signals need to be visually rechecked. Accordingly, although the validation is an automatic inspection, it actually requires substantial manpower.

The conventional computer system, into which all functions are integrated, has many functions that are seldom used. The addition of the useless functions raises the total cost of the system. When the computer system starts up, it authenticates the user. Thereafter, even if another person makes an entry into the computer system, the system is kept operating without further user authentication until it is terminated. Thus, it is essentially impossible to determine who has made the entry. This is a problem about the compliance with the GLP and other standards.

SUMMARY OF THE INVENTION

A first object of the present invention is to provide a safety test support system, a safety test support method and a safety test support program that comply reliably with the GLP and other standards by carrying out an inspection for automatically detecting a change that affects the system operation.

A second object of the present invention is to provide a safety test support system, a safety test support method and a safety test support program that make it possible to greatly reduce the system installation and operation costs by packaging only selected functions in the system and excluding needless and less usable functions.

A third object of the present invention is to provide a safety test support system, a safety test support method and a safety test support program that comply reliably with the GLP and other standards by authenticating the users at predetermined intervals while one or more application programs are active.

According to a first aspect of the present invention, a safety test support system is provided for managing data concerning chemical safety tests on a living body to which a chemical has been given. The data include the condition of the body and/or the like. The support system comprises first program storage, an activating means, second program storage and an inspection conducting means. The first program storage stores application programs for the safety tests, which are functionally partitioned according to data items and/or operations. The activating means activates at least one program selected from the application programs. The second program storage stores check programs each for detecting a change or changes in one of the application programs during the system operation. The inspection conducting means detects changes in the application programs by sequentially executing the stored check programs in response to an inspection conducting signal.

According to a second aspect of the present invention, a safety test support method is provided for managing data concerning chemical safety tests on a living body to which a chemical has been given. The data include the condition of the body and/or the like. The support method comprises the steps of:

storing application programs for the safety tests, which are functionally partitioned according to data items and/or operations, in first program storage;

activating, by means of an activating means, at least one program selected from the application programs;

storing, in second program storage, check programs each for detecting a change or changes in one of the application programs during the system operation; and detecting changes in the application programs by means of an inspection conducting means by sequentially executing the stored check programs in response to an inspection conducting signal.

According to a third aspect of the present invention, a safety test support program is provided for managing data concerning chemical safety tests on a living body to which a chemical has been given. The data include the condition of the body and/or the like. The support program comprises the steps of:

storing application programs for the safety tests, which are functionally partitioned according to data items and/or operations, in first program storage;

activating, by means of an activating means, at least one program selected from the application programs;

storing, in second program storage, check programs each for detecting a change or changes in one of the application programs during the system operation; and detecting changes in the application programs by means of an inspection conducting means by sequentially executing the stored check programs in response to an inspection conducting signal.

The application programs, which are functionally partitioned according to data items and/or operations, are independent of each other. If part of the independent application programs are upgraded or updated, there is no need to inspect the whole system, but it is possible to inspect only the upgraded or updated program/s by executing the associated check program/s. This greatly facilitates the inspection and/or validation during the system operation, so that the inspection can be reliable. It is possible to automatically inspect and/or validate the whole system by sequentially and automatically executing the check programs for the application programs. This makes it possible to quickly and easily inspect and/or validate the whole system. Accordingly, for example, every time the support system is updated with a security patch applied to the operation system, it is possible to reliably carry out the auto-validation of the support system. Because the inspection and/or validation of the whole system can be carried out quickly and easily, it is possible to safely operate the support system by inspecting it after quickly updating it when it is supplied with a security patch or the like. Thus, the support system is easily inspected and/or validated every time it is upgraded and/or updated, and it detects any changes due to the upgrading and/or updating during the system operation. Consequently, the support system can reliably comply with the GLP and other standards. Because the application programs, which are functionally partitioned according to data items and/or operations, are independent of each other, there is no need to introduce less usable and needless applications, so that the system installation and operation costs can be greatly reduced.

If a change that does not affect the system operation is detected in one of the application programs during the system operation, the associated check program may ignore the change. If a change that affects the system operation is detected in one of the application programs during the system operation, the associated check program may regard the change as a change. In this case, the support system does not output all changes as N.G. signals as is the case with the conventional systems, but the check program ignores slight changes of fonts, display color and/or the like that do not at all affect the system operation complying with the GLP and other standards. This makes it possible to greatly reduce the visual reconfirmation of N.G. signals.

The inspection conducting means may inspect the application programs by identifying the application program associated with each of the check programs, inputting a pseudo-signal directly to the identified application program, detecting a response signal responsive to the input pseudo-signal and comparing the detected response signal with a response signal detected before the inspection. By inputting the pseudo-signal directly to the application program, it is possible to detect a pure system change including no factor resulting from the input device and/or driver. Accordingly, even if the input device and/or driver is changed, the system operation and/or inspection is not affected, so that the support system is kept easy to use.

If the pseudo-signal is input to the application program directly without passing through the operation system of the support system, it is possible to detect a pure system change including no factor resulting not only from the input device and/or driver but also from the operation system. If the pseudo-signal is input to the application program through the operation system, it is possible to detect the change in the support system, inclusive of the operation system.

The safety test support system may further comprise a displaying means, a program selecting means, an activation confirming means and a user authenticating means. The displaying means displays a list of the application programs stored in the first program storage. The program selecting means selects one or more of the displayed application programs. The activating means activates the selected application program/s. The activation confirming means confirms at predetermined intervals whether the activated application program or any of the activated application programs is active. The user authenticating means requests at predetermined intervals that authentication information on the user of the support system be input while the activation confirming means is confirming whether the activated program or any of the activated programs is active. In this case, the user is authenticated when the support system is activated and thereafter at the predetermined intervals while the activated application program or any of the activated application programs is active. Consequently, even if another person makes an entry into the support system after the support system is activated, it is essentially possible to determine who has made the entry. This makes it possible to comply reliably with the GLP and other standards.

The safety test support system may further comprise an authentication information holding means for holding validity information on the user authentication by the user authenticating means. When each of the selected application programs is activated, the execution of the activated program may be started if the user authentication is valid, and the execution of the activated program may not be started if the user authentication is invalid, on the basis of the held validity information. In this case, if the user authentication is valid, no user authentication is carried out when each of the selected application programs is activated. This avoids double authentication, thereby making the support system easy to use.

When one or more of the registered application programs are activated, it or they may confirm whether the user authenticating means is active. If the user authenticating means is inactive, it may be activated. In this case, the single authenticating means can manage the authentication of two or more application programs. Accordingly, while part of the selected application programs are active, there is no need to authenticate the user when each of the other programs is activated. Consequently, the working efficiency is improved. While one or more application programs not registered are executed, the user authenticating means is not activated. This prevents the memory capacity from being wasted. Consequently, the execution speed does not fall.

The support system may be used for a chemical toxicity test on an animal as a living body. Such a toxicity test requires an enormous amount of various data. For many such tests, different users of the support system need different types of data. In this case, only usable and necessary application programs may be introduced into the support system, so that the cost of the whole system can be greatly reduced. For such a test, because two or more observers may enter data into the support system by turns, the effect of confirming at regular intervals who has made an entry or entries into the system is remarkable.

BRIEF DESCRIPTION OF THE DRAWINGS

FIG. 2 shows a display screen of the displaying means of the support system.

DETAILED DESCRIPTION OF THE PREFERRED EMBODIMENT

Embodiment 1

Figure 1:
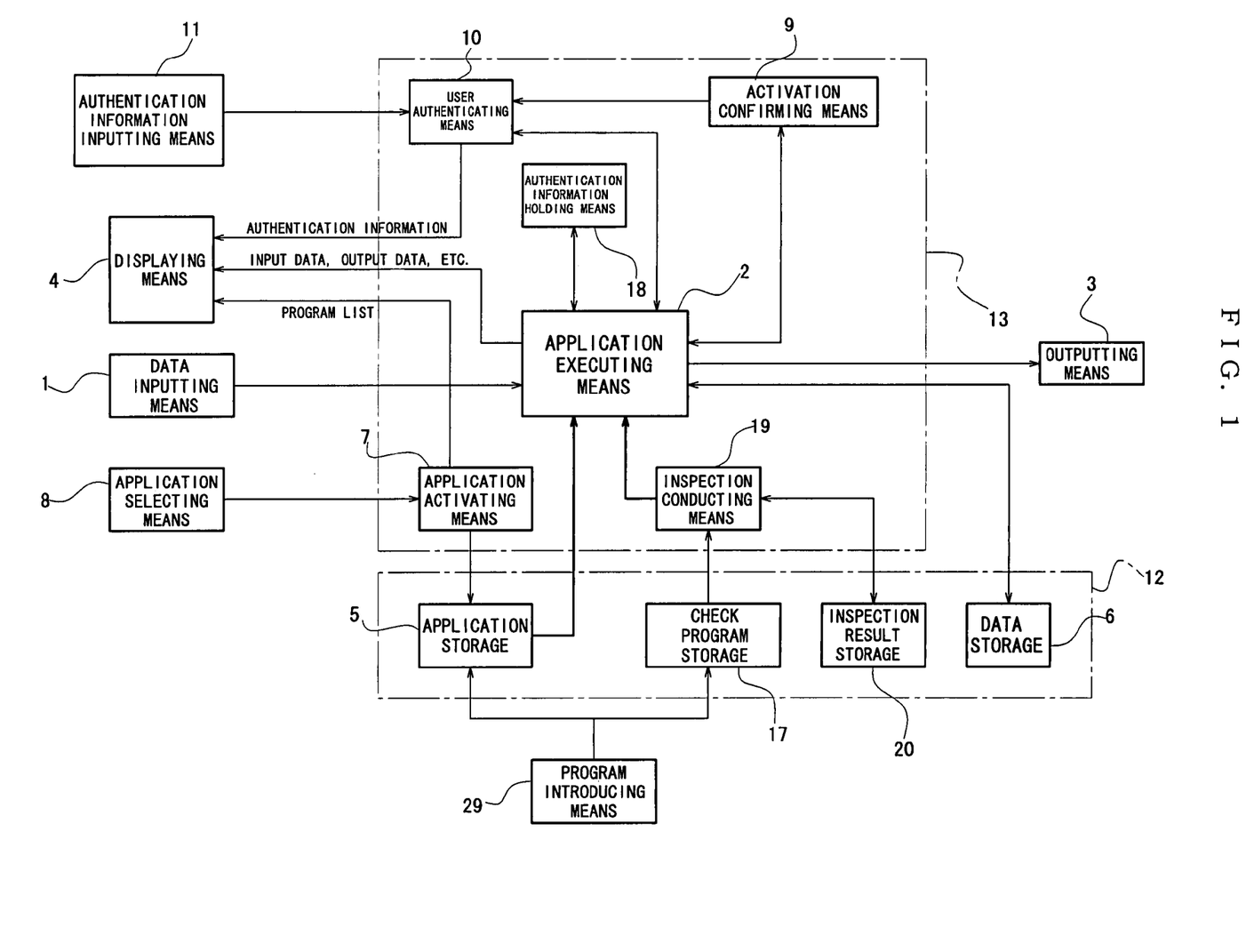
FIG. 1 is a block diagram of a safety test support system according to an embodiment of the present invention.

FIG. 1 shows a safety test support system according to an embodiment of the present invention. The support system is a chemical test data management system, to which the invention is applied. The support system includes a data inputting means 1, an application executing means 2, an outputting means 3, a displaying means 4 and data storage 6.

Data on an animal to which a chemical has been actually given can be entered into the data inputting means 1. The data include body weight, food consumption, water consumption, urinary output, biochemical test results, hematological test results, clinical symptom observation results, pathological opinions (findings or observations), etc. The application executing means 2 receives the data from the inputting means 1 and executes various applications (application programs), which will be described later on, to accumulate and/or otherwise process the data.

The outputting means 3 may be a printer, which outputs the data accumulated or otherwise processed by the application executing means 2 and/or other information on sheets or the like. The displaying means 4 may be a display, which displays various sorts of information when data are entered into and output from the support system. The data storage 6 receives the entered data from the executing means 2 and stores them.

The support system includes a memory unit 12 and an arithmetic unit 13. The memory unit 12 includes a hard disc and an MO. The arithmetic unit 13 includes a CPU and a memory.

The means mentioned above carry out normal entry, accumulation, etc. of data. The data entered into the data inputting means 1 are stored through the application executing means 2 in the data storage 6. During the data entry, the entered data and necessary information are displayed on the displaying means 4. When the entered data are accumulated or otherwise processed, the accumulated or processed data are output from the outputting means 3, and the output data and necessary information are displayed on the displaying means 4.

The support system also includes application storage 5, which functions as the first program storage of the present invention, for storing business applications. The business applications are functionally partitioned according to data items and/or operations, which may be the entry and accumulation of body weight, the output of the accumulated data on body weight, and the entry, accumulation and output of pathological opinions. The business applications can be stored in the application storage 5 at any time by a program introducing means 29, which may be a CD-ROM drive.

The support system further includes an application activating means 7, in which the business applications stored in the application storage 5 are registered. The activating means 7 activates one or more business applications selected out of the registered applications by the user. The storage locations in the application storage 5 where the business applications are stored are associated with the registration locations in the activating means 7 where the respective programs are registered.

A list of the business applications registered in the activating means 7 can be displayed on the displaying means 4. The support system further includes an application selecting means 8, with which the user selects from the list one or more business applications that he or she wants to activate.

The application selecting means 8 may be a mouse or another input device. As shown in FIG. 2, the displaying means 4 has a screen 16, on which a menu 14 can be displayed. The user can select out of the business applications listed in the menu 14 one or more programs that he or she wants to activate. Then, the user can click the icon or icons 15 of the selected program/s, with the pointer (not shown) put on the icon. Only one business application may be activated. Alternatively, two or more business applications may be activated and executed at the same time. On the basis of the related information mentioned above, the application activating means 7 activates the business application/s selected with the application selecting means 8. The application activation includes the steps of reading the business application/s from the application storage 5 into the memory, developing them and obtaining execution authority from the operation system. The application executing means 2 executes the activated application/s.

The support system further includes an act ivati on confirming means 9, which confirms at regular intervals (for example, of 5 minutes) whether the business application or applications activated by the activating means 7 and being executed by the executing means 2 are kept active. The activation confirmation involves inquiring of the operation system whether the application or applications are being developed on the memory and executed.

The support system further includes a user authenticating means 10, which requests the entry of authentication information on the user at regular intervals (for example, of 30 minutes) while the activation confirming means 9 is confirming whether the business application or applications are kept active. The support system further includes an authentication information inputting means 11, with which the user enters authentication information on him or her in response to the request by the authenticating means 10. The authentication time during which the entry of authentication information is requested is set at a period longer than the activation confirmation time during which it is confirmed whether the business application or applications are kept active.

The entry request may involve displaying on the displaying means 4 a password entry screen, which prompts the user to enter his or her password. The authentication information inputting means 11 may be a keyboard or another device, with which the password can be entered on the password entry screen.

When one or more of the business applications registered in the activating means 7 are activated, it or they may confirm whether the authentication program, which is the user authenticating means 10, is activated. If the activation confirming means 9 is inactive, it may be activated by the active application/s. This enables the single authenticating means 10 to manage the authentication of two or more business applications. Accordingly, while part of the business applications are active, there is no need for the user to enter his or her password or be otherwise authenticated when each of the other applications is activated. Consequently, the working efficiency is improved. While any of the business applications not registered are executed, the activation confirming means 9 is not activated. This prevents the memory capacity from being wasted. Consequently, the execution speed does not fall.

The business application or applications being executed by the executing means 2 activate the authentication program, which is the user authenticating means 10. The support system further includes an authentication information holding means 18, which holds the authentication information as to whether the authentication by the user authenticating means 10 is valid or invalid. The business application or applications communicate with the authentication program so that the support system can determine whether to keep executing the application itself or the applications themselves. In order for the authentication program itself not to be activated many times, it determines by itself whether it is terminated.

Figure 3:
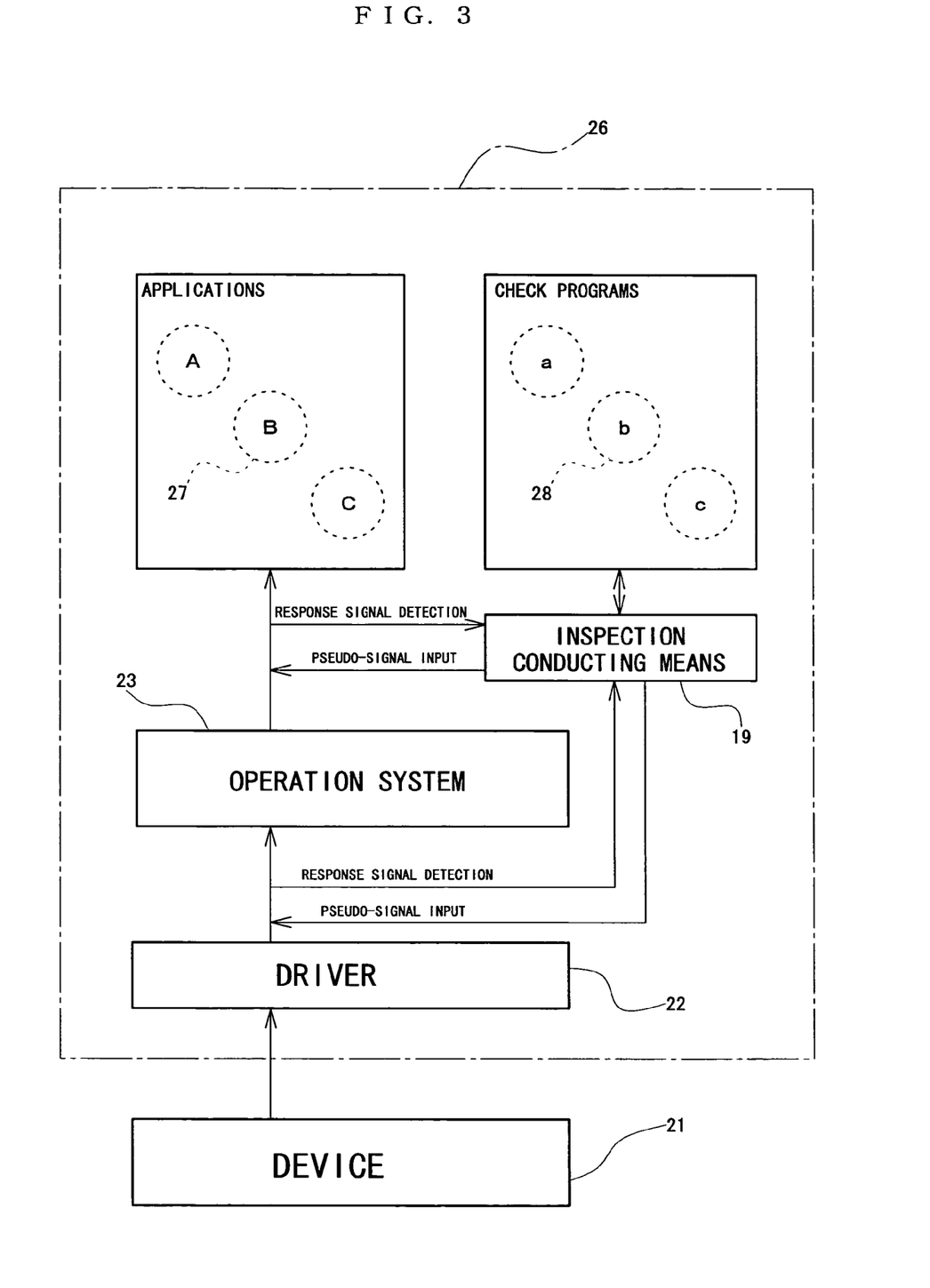
FIG. 3 shows the operation of the support system.

The support system further includes a check program storage 17, which functions as the second program storage of the present invention. The program storage 17 stores check (inspection) programs, each of which is associated with one of the business applications so as to detect the changes in the associated application during the system operation. The support system further includes an inspection conducting means 19, which detects the changes in the business applications by sequentially executing the check programs in the program storage 17 if an inspection conducting signal is input from the mouse and/or the keyboard. As shown in FIG. 3, each of the business applications 27 is associated with one of the check programs 28. In the example shown in FIG. 3, the business applications 27 are applications A, B and C, and the check programs 28 are programs a, b and c, which are associated with the applications A, B and C, respectively.

The business applications 27 and check programs 28 can be introduced suitably from the program introducing means 29. For example, when a business application 27 is introduced as a supplement during the system operation, a check program 28 associated with it is introduced at the same time. Thus, the business applications 27 and check programs 28 are introduced and used always in pairs.

Thus, the business applications 27, which are functionally partitioned according to the data items and/or operations, are independent of each other. Even if part of the business applications 27 are upgraded or updated, it is possible to inspect the upgraded or updated application/s by executing only the associated check program/s 28 without inspecting the whole support system. This greatly reduces the time and labor required by the inspection and/or validation during the system operation, thereby making the inspection reliable. By sequentially and automatically executing check programs 28, which are associated with the respective applications 27, it is possible to automatically carry out the inspection and/or validation of the whole support system, thereby making it possible to quickly and easily carry out the inspection and/or validation of the whole support system. Accordingly, for example, every time the support system is updated with a security patch applied to the operation system, it is possible to reliably carry out the automatic inspection of the support system.

As stated above, it is possible to quickly and easily carry out the inspection and/or validation of the whole support system. Accordingly, if a security patch or the like is supplied, the support system can be inspected after it is quickly updated. This makes it possible to safely operate the support system. Thus, by carrying out the inspection and/or validation of the support system every time the system is upgraded and/or updated, and by detecting any change in the business application/s due to the upgrading and/or updating during the system operation, it is possible to comply reliably with the GLP and other standards. As stated above, the business applications 27 are functionally partitioned according to the data items and/or operations. Accordingly, there is no need to introduce less usable and needless business applications 27. This makes it possible to greatly reduce the system installation and operation costs.

As shown in FIG. 3, the inspection by the inspection conducting means 19 includes the steps of identifying the business application 27 associated with each check program 28, inputting a pseudo-signal directly for the identified application 27, detecting a response signal responsive to the input signal, and comparing the detected signal with that detected before the inspection. An ordinary actuating signal can be entered with the input device 21, which may be the mouse or the keyboard. The input device 21 generates a physical signal, which is then converted into a meaningful signal by the driver 22 for the input device 21. The meaningful signal is input to the business application 27 through the operation system 23. Normally, the check program 28 causes the inspection conducting means 19 to generate a pseudo-signal similar to the actuating signal input from the input device 21 and converted by the driver 22. The pseudo-signal is input to the business application 27 directly or through the operation system 23. The check program 28 detects a response signal representing the response of the business application 27 to the input pseudo-signal. The check program 28 compares the detected response signal with the response signal stored in an inspection result storage 20 before the inspection. If the two response signals differ from each other, the check program 28 causes an N.G. signal to be output. If the response signals are identical, the check program 28 ignores the response signal detected during the inspection and continues the inspection.

Thus, by inputting the pseudo-signal directly to the business application 27, it is possible to detect a pure-system change including no factor resulting from the input device 21 and/or driver 22. Accordingly, even if the input device 21 and/or driver 22 is changed, the system operation and/or inspection is not affected, so that the support system is kept easy to use.

The pseudo-signal may be input directly to the business application 27 without passing through the operation system 23. This makes it possible to detect a pure system change including no factor resulting not only from the input device 21 and/or driver 22 but also from-the operation system 23.

Alternatively, the pseudo-signal may be input to the business application 27 through the operation system 23. This makes it possible to detect the change in the support system, inclusive of the operation system 23. Accordingly, even if the support system is updated with a security patch applied to the operation system, it is possible to detect the system change with the updating taken into consideration, thereby making it possible to comply reliably with the GLP and other standards. Thus, after the operation system 23 is frequently updated, the support system is inspected. This makes it possible to safely operate the support system.

If the check program 28 detects a system change not affecting the system operation, it ignores this change. If the check program 28 detects a system change affecting the system operation, it detects this change as a change.

As stated above, the response signal represents the response of the business application 27 to the input pseudo-signal. The determination of whether there is a change or not (OK or N.G.) in the response signal involves setting a reference range as the basis for determining whether this signal has changed from the previous system state. If the response signal falls within the reference range, it is determined that the signal has not changed (OK). If the response signal exceeds the reference range, it is determined that the signal has changed (N.G.).

For example, the change in the response signal may be a slight change in font size or display color, which does not affect the system operation at al I. If all such changes were detected as N.G. signals, the output of N.G. signals would be enormously frequent, and the N.G. signals would need to be processed visually and manually after all. Therefore, all system changes are not detected as N.G. signals as is the case with the conventional support system. Instead, the reference range is set, and the check program 28 ignores slight changes of fonts, display color and/or the like within this range, which do not at all affect the system operation complying with the GLP and other standards. This makes it possible to greatly reduce the visual reconfirmation of N.G. signals.

Figure 4:
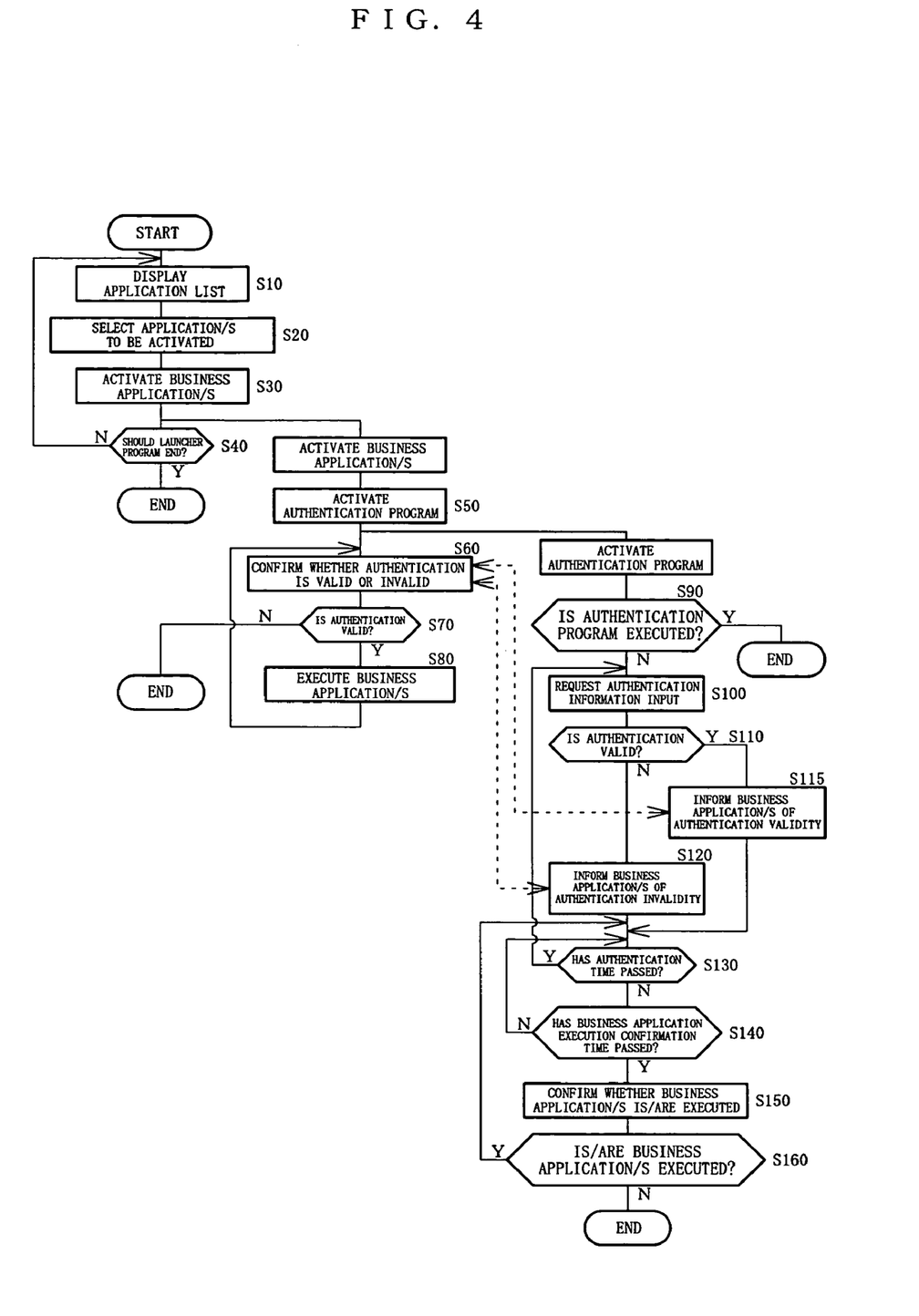
FIG. 4 is a flowchart of the operation of the support system.

FIG. 4 is a flowchart showing the operation of the support system. In the flowchart, each step number follows "S".

When the support system is installed, an acceptance inspection is started. The acceptance inspection includes the steps of entering body weight, food consumption, water consumption, urinary output, pathological opinions and other data through the data inputting means 1, which is the input device 21, causing the application executing means 2 to accumulate or otherwise process the input data so as to confirm that accurate accumulation results can be obtained. The inspection also includes the step of causing the inspection conducting means 19 to execute the check programs 28 so as to confirm whether they can normally operate.

In the meantime, the inspection result storage 20 stores the data input and accumulated and the operation results during the acceptance inspection. At the same time, a reference range is set for each of the operation results.

After the acceptance inspection, actual system operation is started. For normal business, the system operation is continued without the support system validated. During normal system operation, the support system operates as follows.

The first step 10 is to display the list of registered programs on the displaying means 4 (FIG. 2) by starting the launcher program, which is the application activating means 7. The next step 20 is to select one or more of the business applications by clicking the associated icon/s 15 in the menu 14 on the screen 16 of the displaying means 4. The next step 30 is to start activating the selected application/s. Then, the application executing means 2 executes the activated application or applications, inputting body weight, food consumption, water consumption, urinary output, pathological observations and other data, accumulating the input data, outputting the accumulated data onto sheets, and carrying out other processing required for the application/s. The next step 40 is to determine whether to terminate the launcher program. If the launcher program should not be terminated, the routine returns to the step 10. If this program should be terminated, the routine ends.

When the activation of the selected business application/s is started at the step 30, the activation of the authentication program, which is the activation confirming means 9, is started at the step 50. The activation of the authentication program is followed by the step 90 of confirming whether this program is already executed. If the authentication program is already executed, the activation of the authentication program is terminated so that double activation can be prevented. If this program is not executed yet, the step 90 is followed by the step 100.

The step 100 is to request the authentication information inputting means 11 to input authentication information, which may be a password and user ID. The next step 110 is to determine whether the input information is valid. If the authentication information is valid, the step 110 is followed by the step 115 of informing the business application/s of the validity and holding information about the validity in the authentication information holding means 18. If the accurate password is not entered, so that the authentication information is invalid, the step 110 is followed by the step 120 of informing the business application/s of the invalidity and holding information about the invalidity in the holding means 18.

If the entered password is wrong, or if the entered authentication information is not accurate at the step 110, the authentication information inputting means 11 might be requested again to input authentication information. Even after a certain number of entry requests, the accurate password may not be entered, so that the user may not be authenticated. In this case, the halting application or applications might be instructed to forcedly terminate so that it or they could be terminated in response to the termination instruction.

The next step 130 is to wait until an authentication time, which may be 30 minutes, for the authentication of the user passes. If the authentication time has passed, the routine returns to the step 100, where the authentication information inputting means 11 is requested again to input authentication information. If the authentication time has not passed, the step 130 is followed by the step 140 of determining whether a confirmation time for the confirmation of the execution of the business application/s has passed. If the confirmation time has not passed, the routine returns to the step 130, where the foregoing operation is repeated after the authentication time passes again. If the confirmation time has passed, the step 140 is followed by the step 150 of confirming whether the business application or applications are already executed. If the business application or applications are already executed at the step 160, the routine returns to the step 130, where the foregoing operation is repeated after the authentication time passes again. If no business application is executed at the step 160, the authentication program is terminated.

In the meantime, after the activation of the selected business application/s is started at the step 30, and then the activation of the authentication program is started at the step 50, the routine goes to the step 60. The step 60 is to confirm, by communicating with the authentication program, whether the authentication information held by the holding means 18 is valid or invalid.

If the authentication information held by the holding means 18 is valid at the step 70, this step is followed by the step 80 of executing the active business application/s. If this information is invalid, the activation of the selected business application/s ends.

Thus, while the activated application or any of the activated applications is active, the user is authenticated at regular intervals. This makes it essentially possible to determine who makes an entry or entries into the support system. Consequently, the support system can comply reliably with the GLP and other standards. The business applications, which are functionally partitioned according to the data items and/or operations, are independent of each other. If part of the business applications are upgraded or updated, it is possible to validate only the upgraded or updated application/s. This makes it possible to comply reliably with the GLP and other standards by means of reliable validation during the system operation. There is no need to introduce less usable and need less applications, so that the cost of the whole system can be greatly reduced.

When the support system is activated, the user is authenticated. Thereafter, another person may make an entry into the support system. While any of the activated applications is active, the user is authenticated at regular intervals. This makes it essentially possible to determine who has made the entry. Consequently, the support system can comply reliably with the GLP and other standards. Once the authentication program authenticates the user, it carries out no user authentication when each business application is activated. This avoids double authentication, thereby making the support system easy to use.

The single user authenticating means can manage the authentication of a number of applications. Accordingly, while part of the applications are active, there is no need to authenticate the user when each of the other applications is activated. This improves the working efficiency. While any of the applications not registered are executed, the user authenticating means is not activated. This prevents the memory capacity from being wasted. Consequently, the execution speed does not fall.

The support system is suitable for a chemical toxicity test on an animal as a living body. Such a toxicity test requires an enormous amount of various data. In many cases, different users of the support system need different types of data for the test. Accordingly, it is possible to introduce only usable and necessary programs into the support system, so that the cost of the whole system can be greatly reduced. In many cases, two or more observers enter data into the support system by turns for the test. Consequently, the effect of confirming at regular intervals who enters data into the support system is remarkable.

Figure 5:
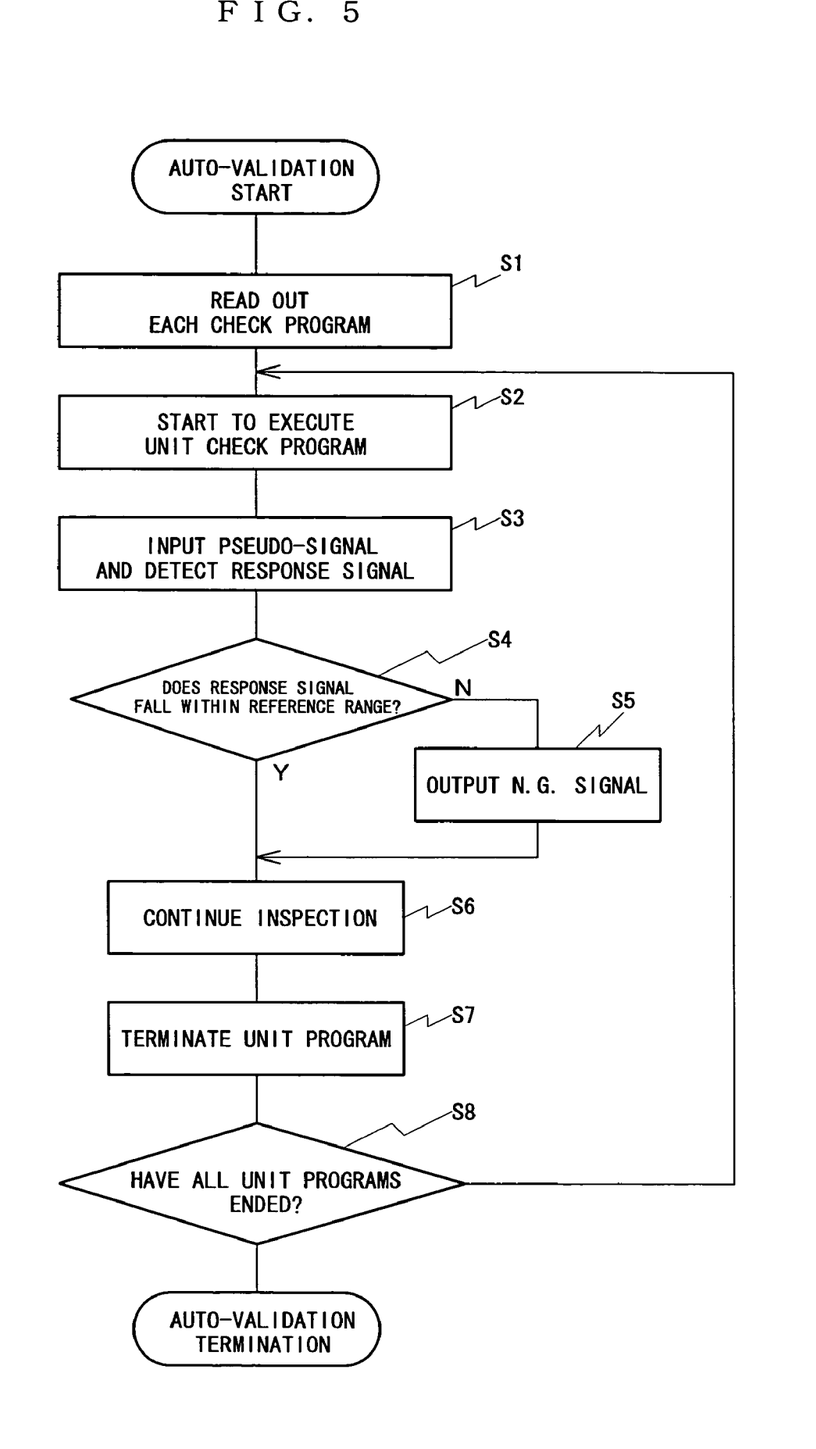
FIG. 5 is another flowchart of the operation of the support system.

FIG. 5 is a flowchart showing the auto-validation carried out in the support system. In the flowchart, each step number follows "S".

The auto-validation may include the following steps:

1. Design Qualification (DQ): requirements specifications, functional specifications, performance specifications and maker selection criteria before the equipment is purchased, or when the purpose of use is changed 2. Installation Qualification (IQ): checks with invoices and the confirmation of hardware and software installation when the hardware or software is installed, or after the support system is upgraded or moved
3. Operational Qualification (OQ): important functions before each routine is used, or one or more times a year
4. Performance Qualification (PQ): the performance for each purpose of use, preventive maintenance, and the confirmation of the operating performance of the support system in operation before or while each routine operates, or everyday, or while the system is used The important validation steps are not only the installation qualification (IQ) but also the qualification during the system operation (OQ and PQ). For example, if the support system is cooperative with Excel, it requires qualification for a new version of Excel. Even if the support system is not cooperative with Internet Explorer, it requires qualification if Internet Explorer is updated. Such a system that is validated when it is changed cannot cope with the changes of which the user is not aware. A TOX launcher can periodically perform automatic validation. Specifically, the function of recording and/or programming a validation procedure and making a decision as a result is added.

The first step 1 is to read the check programs 28 from the check program storage 17 in response to an inspection conducting signal input from the input device 21, which may be the mouse or the keyboard. The next step 2 is to start executing the first unit check program a out of the read programs 28 (FIG. 3). At the next step 3, the executed program "a" causes a pseudo signal to be input to the application A, which is associated with this program, and the response signal output in response to the pseudo signal by this application to be detected.

Subsequently, the detected response signal is compared with the inspection result stored in the inspection result storage 20. The comparison determines whether there is a change during the system operation. The determination includes the step 4 of determining whether the response signal falls within the reference range set during the first acceptance inspection. If the response signal falls within this range, it is ignored as a change that does not affect the system operation. Then, the step 4 is followed by the step 6 of executing the inspection. If the response signal exceeds the range, it is regarded as a change that affects the system operation. Then, the step 4 is followed by the step 5 of outputting a N.G. signal. The step 5 is followed by the step 6 of executing the inspection. The N.G. signal represents the application name, the place and content of the change, etc., which may be specified on the displaying means 4, which may be the display, or output by the outputting means 3, which may be a printer.

The step 7 is to terminate the first unit check program "a". After the program termination, the present validation and comparison results are output from the outputting means 3 and stored in the inspection result storage 20. The next step 8 is to determine whether all the unit programs (a, b and c in FIG. 3) have ended. If all the programs have not ended, the routine returns to the step 2, where the execution of the second unit program "b" is started. If all the programs have ended, the auto-validation is terminated.

Thus, by automatically performing all the validation after the first validation, it is possible to terminate the validation in less then one night, which has conventionally taken two or three people three or more months. Accordingly, it is possible to comply reliably with the GLP and other standards by performing not only the periodic validation during the system operation but also frequent validation at a time when the operation system or noncooperative software is updated. The diligent validation makes it possible to use a general purpose computer, greatly reducing the system installation cost.

The procedure of the validation performed inevitably during the acceptance inspection is stored, and the validation after the first validation is performed. Accordingly, even if the support system is not uniformly packaged but customized for the buyer, the validation necessary for the buyer can be performed automatically after the first validation.

The support system is suitable for a chemical toxicity test on an animal as a living body. Because such a toxicity test requires an enormous amount of various data, it is required that the system installation cost be low, and the effect of using a general purpose computer is remarkable.

The application of the support system is not limited to chemical toxicity tests on animals. The support system might also be applied, with similar effects, to medicinality/pharmacological tests and/or general pharmacological tests prior to safety tests on animals, pharmacokinetic tests, clinical tests to which GCP (standards for the conduction of clinical tests of medicines or pharmaceuticals) is applied, and/or non-GLP tests.

The chemicals are not limited to medicines or pharmaceuticals, but include agricultural chemicals, food additives, ointments and/or other applications, and/or other chemical substances.

The process for activating one or more programs (steps 10-40), the process for confirming the activation (steps 90-160), the process for activating one or more business applications (steps 50-80) and other processes have been described as a series of routines. Alternatively, these processes might be executed asynchronously in independent forms.

The entry of authentication information is the entry of a password with the keyboard. Alternatively, authentication information might be entered by means of a magnetic card, an IC card or another ID card, or a fingerprint, voiceprint or retina recognition system.

What is claimed is:

1. A safety test support system for managing data concerning at least one of medicines, pharmaceuticals, agricultural chemicals, food additives or other chemical safety tests on a living body to which at least one of a medicine, pharmaceutical, agricultural chemical, food additive or other chemical has been given, the data including the condition of the living body, measuring of at least one of the living body's weight, food consumption, water consumption, urinary output, biochemical test results, hematological test results, clinical symptom observation results pathological opinions based upon findings and/or observations about the living body, the system comprising:

first program storage for storing application programs for the safety tests, the programs being functionally partitioned according to data items and/or operations;

an activating means for activating at least one program selected from the application programs;

second program storage for storing check programs each for detecting a change in one of the application programs during the system operation; and an inspection conducting means for detecting changes in the application programs by sequentially executing the stored check programs in response to an inspection conducting signal wherein the safety test support system is constructed so that: a) if a change that does not affect the system operation is detected in one of the application programs during the system operation, the associated check program ignores the change; and b) if a change that affects the system operation is detected in one of the application programs during the system operation, the associated check program regards the change as a change.

2. The safety test support system according to claim 1 wherein the inspection conducting means inspects the application programs by:

identifying the application program associated with each of the check programs;

inputting a pseudo-signal directly to the identified application program; detecting a response signal responsive to the input pseudo-signal; and     comparing the detected response signal with a response signal detected before the inspection.

3. The safety test support system according to claim 2 wherein the pseudo-signal is input without passing through an operation system.

4. The safety test support system according to claim 2 wherein the pseudo-signal is input through an operation system.

5. The safety test support system according to claim 1 and further comprising:

a displaying means for displaying a list of the application programs stored in the first program storage;

a program selecting means for selecting one or more of the displayed application programs;

the activating means being adapted to activate the selected application program or programs;

an activation confirming means for confirming at predetermined intervals whether the activated application program or any of the activated application programs is active; and     a user authenticating means for requesting at predetermined intervals that authentication information on the user of the support system be input while the activation confirming means is confirming whether the activated program or any of the activated programs is active.

6. The safety test support system according to claim 5 and further comprising an authentication information holding means for holding validity information on the user authentication by the user authenticating means, wherein, when each of the selected application programs is activated, the execution of the activated application program is started if the user authentication is valid, and the execution of the activated application program is not started if the user authentication is invalid, on the basis of the held validity information.

* * * * *